United States Patent [19]

Lavender

[11] Patent Number: 4,980,068
[45] Date of Patent: Dec. 25, 1990

[54] SYSTEM, APPARATUS AND METHOD FOR CONTINUOUSLY FRACTIONATING BLOOD IN SITU

[76] Inventor: Ardis R. Lavender, 15 Deerfield Rd., Chappaqua, N.Y. 10514

[21] Appl. No.: 523,007

[22] Filed: Aug. 15, 1983

[51] Int. Cl.[5] ............................................. B01D 6/18
[52] U.S. Cl. ............................... 210/651; 210/321.84; 210/456
[58] Field of Search ...................... 210/927, 651, 433.6, 210/456, 137, 321.84; 604/4, 5, 6

[56] References Cited

U.S. PATENT DOCUMENTS

| | | | |
|---|---|---|---|
| 3,705,100 | 12/1972 | Blatt et al. | 210/456 X |
| 4,110,220 | 8/1978 | Lavender | 210/456 X |
| 4,162,982 | 7/1979 | Chesner | 210/347 X |
| 4,212,742 | 7/1980 | Solomon et al. | 210/433.2 X |
| 4,318,813 | 3/1982 | Edelman et al. | 210/433.2 X |
| 4,324,658 | 4/1982 | Esmund | 210/456 X |
| 4,375,415 | 3/1983 | Lavender | 210/456 X |
| 4,401,566 | 8/1983 | Igari et al. | 210/927 X |

FOREIGN PATENT DOCUMENTS

| | | |
|---|---|---|
| 0045073 | 2/1982 | European Pat. Off. . |
| 0021301 | 1/1987 | European Pat. Off. . |
| 2112293 | 7/1983 | United Kingdom . |

*Primary Examiner*—Frank Spear
*Attorney, Agent, or Firm*—Emrich & Dithmar

[57] ABSTRACT

A system, method and device for continuously fractionating blood in situ. The fractionating device is connected in a closed loop to the donor and includes interleaved blood plates and blood fraction plates separated by a semipermeable membrane. Grooves in the plates direct blood flow and blood fraction collection. Uniform distribution among the plates and intraplate is obtained by manifolds.

106 Claims, 2 Drawing Sheets

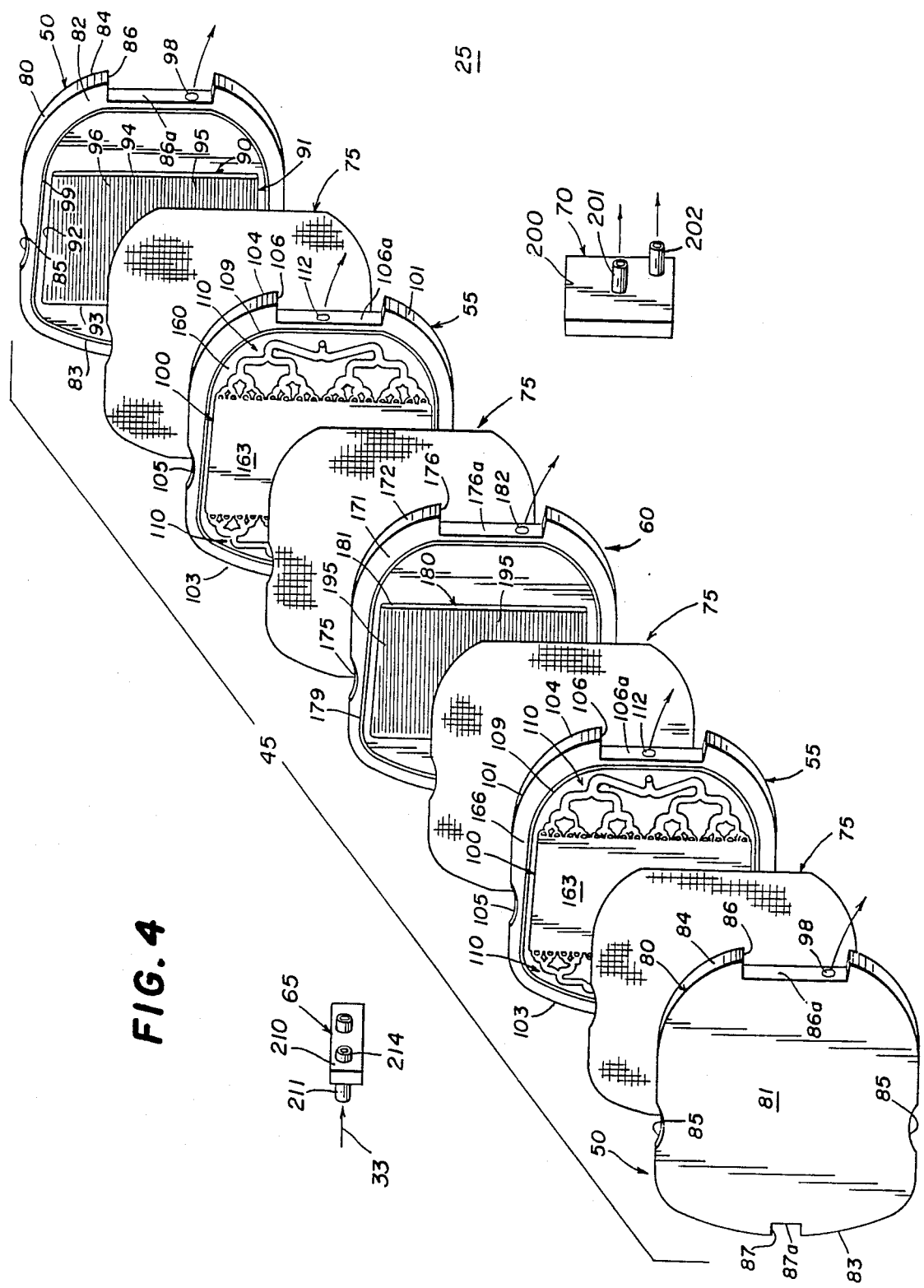

SYSTEM, APPARATUS AND METHOD FOR CONTINUOUSLY FRACTIONATING BLOOD IN SITU

BACKGROUND OF THE INVENTION

There are many reasons for fractionating blood to separate various components thereof, one of the most important being to obtain plasma. Plasma has been found to be efficacious in the treatment of various disease states and is generally useful since it may be stored for long periods in comparison to whole blood which has a rather short shelf life.

When harvesting plasma from a donor, it is preferred to return the formed elements of the blood including red blood cells, white blood cells and platelets to the donor so that frequent plasma harvestings may be effected Traditionally, plasma is harvested by transferring blood from a donor into a blood bag and thereafter centrifuging the blood to separate the plasma from the formed elements of the blood. Then the plasma is separated from the formed elements of the blood, the formed elements are thereafter reconstituted with a saline solution and reintroduced to the donor. Because of a variety of reasons, generally each donor must undergo two such operations for each plasma donation.

The traditional manner of harvesting plasma involves several risks and discomforts to the donor. A principal risk is the chance that the reconstituted blood returned to the donor will not be the donor's, a situation which has in the past resulted in fatalities. Other attendant risks are those of infection and the like. The discomfort involves, among other things, the inordinate length of time required to permit two samples of blood to be taken with the required centrifuging of each sample, the large volume of blood removed for processing, the reconstituting of the formed elements into a saline solution and reintroducing same to the donor It is clear that a simpler, safer, speedier system for harvesting plasma is needed and has been needed for a considerable length of time.

One such proposed alternative to the above-described traditional method of harvesting plasma is described in the Blatt et al. U.S. Pat. No. 3,705,100 issued Dec. 5, 1972, which patent discloses an apparatus and method for harvesting plasma from whole blood which includes a cylinder having a reservoir and on the bottom of the cylinder a spiral flow path formed by a spiral groove which sits on top of a membrane having a predetermined pore size. Blood in the reservoir is forced through the spiral path by means of a pressurized gas driving fluid A second embodiment of the apparatus is disclosed in which a hypodermic syringe is used to withdraw blood from a patient and thereafter introduce the blood into the same sort of spiral flow path as previously described.

The Blatt et al. apparatus and process is not utilized for the commercial production of plasma. The Blatt et al. process and method is, like the described prior art, a batch process and requires withdrawing blood from a donor, treating it and thereafter reintroducing the blood into the donor with all the attendant risks and time delays previously described. Accordingly, none of the serious drawbacks of the prior art have been solved by the Blatt et al. disclosure.

SUMMARY OF THE INVENTION

This invention relates to a system, apparatus and method for continuously fractionating blood in situ The fractionating device, per se, is small and relatively inexpensive in contradistinction to the available prior art devices which are complicated and costly. Most advantageously, the inventive system, apparatus and method permits blood to be taken from a donor and returned to the donor in a closed loop, thereby obviating any chance of returning incorrect blood, reducing the time necessary for plasma harvesting and reducing the cost of the equipment and labor necessary to obtain blood plasma.

An important object of the present invention is to provide a system, apparatus and method for continuously fractionating blood in situ.

Another object of the present invention is to provide a device for continuously producing a blood fraction, comprising a stack of at least two plates having at least one surface with a blood flow channel therein facing a surface with a collection channel therein separated by a semipermeable membrane selectively permeable to the blood fraction, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof, each collection channel being substantially in registry with the transfer portion of the facing blood flow channel for receiving the blood fraction passing through the membrane, and a fraction outlet for conducting the blood fraction from each collection channel, whereby the blood fraction continuously transfers from blood passing through the transfer portion of each blood flow channel through the membrane to the adjacent collection channel to the fraction outlet.

Another object of the present invention is to provide a method of continuously fractionating blood in situ, comprising establishing a closed loop between the blood donor and a device having a blood inlet and outlet and a blood fraction outlet, pumping blood from the donor to the blood inlet and through the device and from the blood outlet to the donor while continuously producing a blood fraction, and collecting the blood fraction from the blood fraction outlet.

Still another object of the present invention is to provide a system for continuously producing a blood fraction in situ comprising a closed blood flow loop between a blood fraction donor and a fractionating device, a pump for pumping blood from the donor to the fractionating device and therefrom to the donor, the fractionating device comprising a stack of at least two plates having at least one surface with a blood flow channel therein facing a surface with a collection channel therein separated by a semipermeable membrane selectively permeable to the blood fraction, an inlet to the device connected to the closed loop for conducting blood to each blood flow channel and an outlet from the device connected to the closed loop for establishing a longitudinally extending blood flow path through the device, each blood flow channel having a distribution portion for uniformly distributing blood transversely of the blood flow path and a transfer portion extending longitudinally thereof, each collection channel being substantially in registry with the transfer portion of the facing blood flow channel for receiving the blood fraction passing through the membrane, a fraction outlet for conducting the blood fraction from each collection channel, and a receptacle for storing the blood fraction, whereby the blood fraction continuously transfers to the receptacle from blood passing through the device during transit from and to the donor in the closed loop.

A still further object of the present invention is to provide a device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof, each plasma collection channel being substantially in registry with the transfer portion of the facing blood flow channel for receiving plasma passing through the membrane, and a plasma outlet for conducting plasma from each plasma collection channel, whereby plasma continuously transfers from blood passing through the transfer portion of each blood flow channel through the membrane to the adjacent plasma collection channel to the plasma outlet.

A still further object of the present invention is to provide a device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof tapered from inlet to outlet to maintain the blood flow velocity and shear substantially constant as plasma is transferred from the blood, each plasma collection channel being tapered and substantially in registry with the tapered transfer portion of the facing blood flow channel for receiving plasma passing through the membrane, and a plasma outlet for conducting plasma from each plasma collection channel, whereby plasma continuously transfers from blood passing through the transfer portion of each blood flow channel through the membrane to the adjacent plasma collection channel to the plasma outlet.

Still another object of the present invention is to provide a device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distribution blood transversely of the blood flow path and a transfer portion extending longitudinally thereof, each plasma collection channel being substantially in registry with the transfer portion of the facing blood flow channel for receiving plasma passing through the membrane, means associated with each plasma collection channel for minimizing transmembrane pressure to reduce the rate at which red blood cells plug the membrane, and a plasma outlet for conducting plasma from each plasma collection channel, whereby plasma continuously transfers from blood passing in the transfer portion of each blood flow channel through the membrane to the adjacent plasma collection channel to the plasma outlet.

Yet another object of the present invention is to provide a device for continuously producing plasma, comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet extending through the end surface of each plate having a blood flow channel therein for conducting blood to the blood flow channel and an outlet extending through the end surface of the plate for conducting blood therefrom to establish a longitudinally extending blood flow path, each of the blood flow channels having a distribution portion for uniformly distributing blood transversely of the blood flow path and a transfer portion extending longitudinally thereof, each of the plasma collection channels being substantially in registry with the transfer portion of the facing blood flow channel for receiving plasma passing through the membrane, and a plasma outlet for conducting plasma from each of the plasma collection channels, whereby plasma continuously transfers from blood passing through the transfer portion of each blood flow channel through the membrane to the adjacent plasma collection channel to the plasma outlet.

Yet another object of the present invention is to provide a device for continuously producing plasma, comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each of the blood flow channels having a distribution portion for uniformly distributing blood transversely of the blood flow path inlet and a transfer portion extending longitudinally thereof and a combining portion for conducting blood from the transfer portion to the outlet, the distribution and the combining portions each comprising a multiple bifurcated manifold wherein the depth of the manifold increases from the transfer portion to the inlet or the outlet, each of the plasma collection channels being substantially in registry with the transfer portion of the facing blood flow channel for receiving plasma passing through the membrane, and a plasma outlet for conducting plasma from each of the plasma collection channels, whereby plasma continuously transfers from blood passing through the transfer portion of each blood flow channel through the membrane to the adjacent plasma collection channel to the plasma outlet.

A still further object of the present invention is to provide a device for continuously producing plasma comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet extending through the end surface of each plate having a blood flow channel therein for conducting blood to the blood flow channel and an outlet extending through the end surface of the plate for conducting blood therefrom to establish a longitudinally extending blood flow path, each of the blood flow channels having a distribution portion for uniformly distributing blood transversely of the blood flow path and a transfer portion extending longitudinally thereof and a combining portion for conducting blood from the transfer portion to the outlet, the distribution and the combining portions each comprising a multiple bifurcated manifold wherein the depth of the manifold increases from the transfer portion to the inlet or the outlet, each plasma collection channel being substantially in registry with the transfer portion of the facing blood flow channel for receiving plasma passing through the membrane and a slot in communication with the plasma collection channel extending transversely thereof, and a plasma outlet in communication with the slots for conducting plasma from the plasma collection channels, whereby plasma continuously transfers from blood passing through the transfer portion of each blood flow channel through the membrane to the adjacent plasma collection channel to the plasma outlet.

Yet another object of the present invention is to provide a device for continuously producing plasma, comprising a stack of plates having a plurality of substantially flat surfaces with some of the surfaces having a blood flow channel therein and the others having a plasma collection channel therein, the facing surfaces in the stack having therein a blood flow channel and a plasma collection channel separated by a semipermeable membrane having a pore size in the range of from about 0.1 microns to about 1.5 microns, a blood inlet extending through the end surface of each plate having a blood flow channel therein for conducting blood to the blood flow channel and a blood outlet extending through the opposite end surface of the plate for conducting blood therefrom to establish a longitudinally extending blood flow path, each of the blood flow channels having a distribution portion for uniformly distributing blood transversely of the blood flow path and a transfer portion extending longitudinally thereof, a blood inlet manifold connected to each blood inlet for distributing blood from a source thereof evenly among said blood inlets and a blood outlet manifold connected to each blood outlet for collecting blood therefrom and combining same into a single stream, each of the plasma collection channels being substantially in registry with the transfer portion of the facing blood flow channel for receiving plasma passing through the membrane, a plasma outlet extending through the end surface of each plate having a plasma collection channel therein for conducting plasma therefrom, and a plasma outlet manifold connected to each plasma outlet for collecting plasma therefrom and combining same into a single stream, whereby plasma continuously transfers from blood passing through the transfer portion of each blood flow channel through the membrane to the adjacent plasma collection channel to the plasma outlet.

A still further object of the present invention is to provide a device for continuously producing plasma, comprising a stack of interleaved blood plates and plasma plates with each blood plate having a blood flow channel in at least one substantially flat surface thereof and with each plasma plate having a plasma collection channel in at least one substantially flat surface thereof, the stack being constructed and arranged such that each surface having therein a blood flow channel faces a surface having therein a plasma collection channel separated by a semipermeable membrane having a pore size in the range of from about 0.1 microns to about 1.5 microns, a blood inlet extending through the end surface of each blood plate for conducting blood to the blood flow channel and a blood outlet extending through the opposite end surface of the plate for conducting blood therefrom to establish a longitudinally extending blood flow path, each of the blood flow channels having a distribution portion for uniformly distributing blood transversely of the blood flow path and a transfer portion extending longitudinally thereof tapered from inlet to outlet to maintain the blood flow velocity and shear substantially constant as plasma is transferred from the blood and a combining portion for conducting blood from the transfer portion to the outlet, the distribution and the combining portions each comprising a multiple bifurcated manifold wherein the depth of the manifold increases from the transfer portion to the inlet or the outlet, a blood inlet manifold connected to the stack and to each blood inlet for distributing blood from a source thereof substantially uniformly among the blood inlets and a blood outlet manifold connected to the stack and to each blood outlet for collecting blood therefrom and combining same into a single stream, each of the plasma collection channels being tapered and substantially in registry with the tapered transfer portion of the facing blood flow channel for receiving plasma passing through the membrane, and each of the plasma collection channels including a plurality of longitudinally extending grooves having a depth of about 3 mils terminating in a transversely extending collection slot, a plasma outlet for conducting plasma from each of the plasma collection slots, and a plasma outlet manifold connected to the stack and to each plasma outlet for collecting plasma therefrom and combining same into a single stream, whereby plasma continuously transfers from blood passing through the transfer portion of each blood flow channel through the membrane to the adjacent plasma collection channel to the plasma outlet.

Yet another object of the present invention is to provide a plate forming a blood flow path from one end to the other comprising, a pair of substantially flat opposed surfaces with at least one surface having a blood flow channel therein, and an inlet for conducting blood to the blood flow channel and an outlet for conducting blood therefrom to establish a longitudinally extending blood flow path, the blood flow channel having a distribution portion for uniformly distributing blood transversely of the blood flow path and a transfer portion extending longitudinally thereof tapered from inlet to outlet.

A still further object of the present invention is to provide a plate forming a blood flow path from one end to the other comprising, a pair of substantially flat opposed surfaces with at least one surface having a blood flow channel therein, and an inlet extending through the end surface of the plate for conducting blood to the blood flow channel and an outlet extending through the opposite end surface of the plate for conducting blood therefrom to establish a longitudinally extending blood flow path, the blood flow channel having a distribution portion for uniformly distributing blood transversely of the blood flow path and a transfer portion extending longitudinally thereof tapered from inlet to outlet.

A still further object of the present invention is to provide a plate forming a blood flow path from one end to the other comprising, a pair of substantially flat opposed surfaces with at least one surface having a blood flow channel therein, and an inlet extending through the end surface of the plate for conducting blood to the blood flow channel and an outlet extending through the opposite end surface of the plate for conducting blood therefrom to establish a longitudinally extending blood flow path, the blood flow channel having a distribution portion for uniformly distributing blood transversely of the blood flow path and a transfer portion extending longitudinally thereof tapered from inlet to outlet and a combining portion for conducting blood from the transfer portion to the outlet, the distribution and the combining portions each comprising a multiple bifurcated manifold wherein the depth of the manifold increases from said transfer portion to the inlet or the outlet.

Yet another object of the present invention is to provide a plate for collecting plasma, comprising a pair of substantially flat opposed surfaces with at least one surface having a plasma collection channel therein, an outlet in fluid communication with the plasma collection channel, the plasma collection channel having a longitudinally extending collection portion and a transversely extending slot at the end of the collection portion connected to said outlet, the slot having a greater depth than the plasma collection portion of the channel.

A final object of the present invention is to provide a plate for collecting plasma, comprising a pair of substantially flat opposed surfaces with at least one surface having therein a plasma collection channel including a plurality of longitudinally extending shallow grooves, an outlet in fluid communication with the plasma collection channel, the plasma collection channel having a plurality of longitudinally extending shallow grooves terminating in a transversely extending slot connected to the outlet, the slot having a greater depth than the shallow grooves.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 4 is an exploded perspective view of the blood fractionating device illustrated in FIG. 1;

FIG. 5 is an enlarged plan view of an internal blood fraction collection plate;

FIG. 6 is an enlarged plan view of a blood plate;

FIG. 7 is a view in section of the collection plate illustrated in FIG. 5 as seen along line 7—7 thereof;

FIG. 8 is a view in section of the collection plate illustrated in FIG. 5 as seen along line 8—8 thereof;

FIG. 9 is a view in section of the collection plate illustrated in FIG. 5 as seen along line 9—9 thereof;

FIG. 10 is an enlarged view of a portion of the collection plate illustrated in FIG. 9;

FIG. 11 is a view in section of the blood plate illustrated in FIG. 6 as seen along line 11—11 thereof;

FIG. 12 is a view in section of the blood plate illustrated in FIG. 6 as seen along line 12—12 thereof;

FIG. 13 is a view in section of the blood plate illustrated in FIG. 6 as seen along line 13—13 thereof;

FIG. 14 is a view in section of the blood plate illustrated in FIG. 6 as seen along line 14—14 thereof;

FIG. 15 is a view in section of the blood fractionating device illustrated in FIG. 2 as seen along line 15—15 thereof;

FIG. 16 is a view in section of the blood fractionating device illustrated in FIG. 2 as seen along line 16—16 thereof;

FIG. 17 is an end elevational view of the outlet manifold of the blood fractionating device illustrated in FIG. 2;

FIG. 18 is a view in section of the blood fractionating device illustrating in FIG. 2 as seen along line 18—18 thereof; and FIG. 19 is an end elevational view of the inlet manifold of the blood fractionating device illustrated in FIG. 2.

DESCRIPTION OF THE PREFERRED EMBODIMENT

Figure 1:
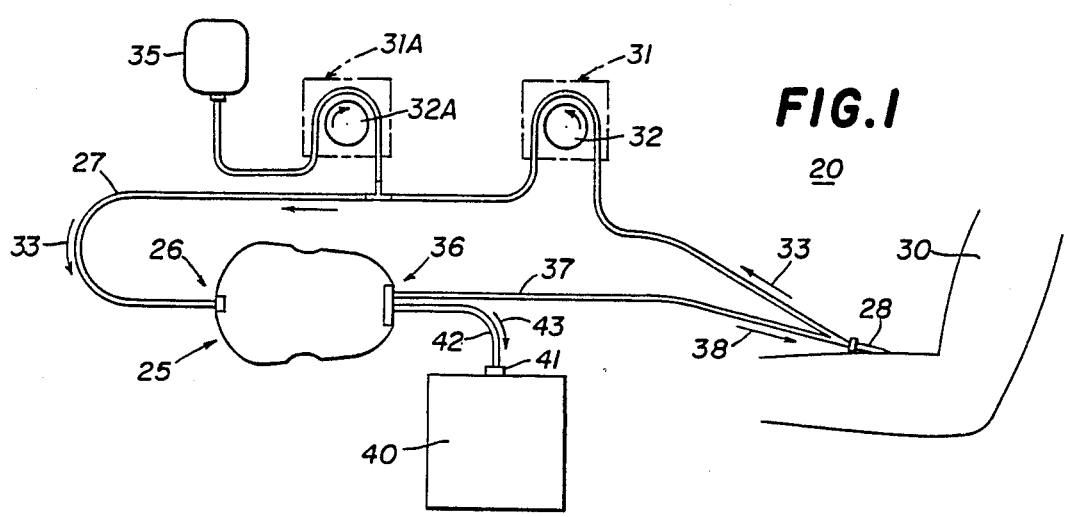
FIG. 1 is a diagrammatic view of the system of the present invention showing the in situ fractionation of blood.

Referring now to FIG. 1 there is illustrated a blood fractionating system 20 which includes a blood fractionator 25 connected in a closed loop to a donor 30. The blood fractionator 25 has an inlet 26 and an outlet 36, the inlet 26 being connected to the donor 30 by a blood tube 27 connected to a catheter, needle or double lumen needle 28 inserted into an appropriate vein or artery of the donor 30. A peristaltic pump 31 having a roller 32 in contact with the blood tube 27 is positioned between the donor 30 and the inlet 26 of the blood fractionator 25 to pump blood from the donor through the tube 27 into the fractionator in the direction of the arrow 33. A supply of anti-coagulant 35 is connected to the tube 27 and the flow rate of the anti-coagulant is modified by a second pump 31A having a roller 32A to provide a predetermined flow rate, as hereinafter explained, of anti-coagulant with the blood flowing from the donor 30 to the fractionator 25. The outlet 36 of the fractionator 25 is provided with a tube 37 which conducts blood in the direction of the arrow 38 to the catheter, needle or double lumen needle 28, thereby to provide the closed loop for the system 20 of the present invention. A blood fraction collection receptacle or bag 40 is provided with a fitting 41 which is connected by a tube 42 to the outlet 36 and more particularly the outlet port 201, see FIG. 15 of the blood fractionator 25 thereby to permit a blood fraction to flow from the outlet 36 in the direction of the arrow 43 to the blood fraction collection bag or receptacle.

Although the blood fractionator 25 of the present invention along with the system 20 disclosed herein may be useful to produce a variety of blood fractions, plasma is one of the most important blood fractions needed in the medical community, and therefore, the blood fractionator 25 as well as the system 20 and method of collecting a blood fraction will hereinafter be described with respect to blood plasma only, it being understood that other blood fractions may be collected with minor modifications to the device 25 and system 20, as will be apparent to those skilled in the art.

Figure 2:
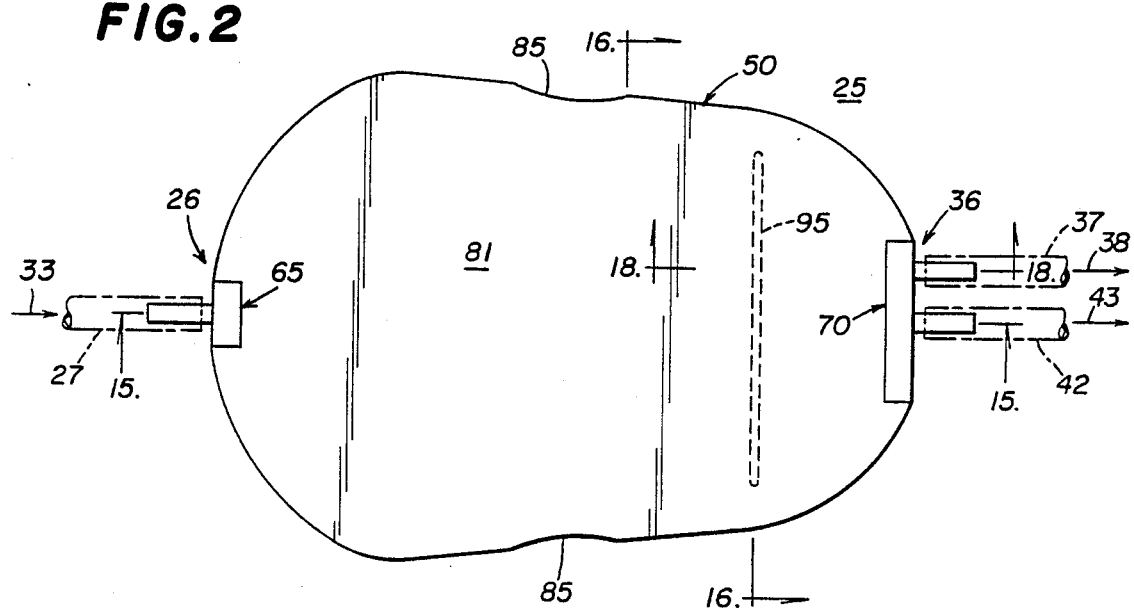
FIG. 2 is an enlarged top plan view of the blood fractionating device illustrated in FIG. 1.
Figure 3:
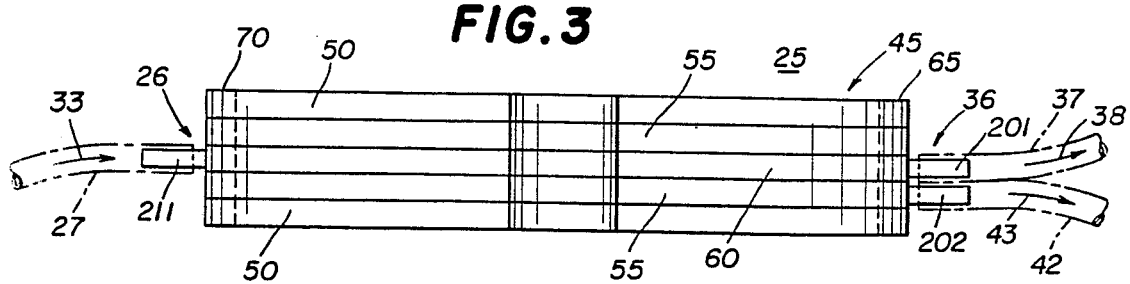
FIG. 3 is a side elevational view of the device illustrated in FIG. 2.

Referring now to FIGS. 2, 3 and 4, it will be appreciated that the blood fractionator 25 is made up of a stack 45 of plates, there being provided two external plasma plates 50 two internal blood plates 55 and an interior or internal plasma plate 60, an appropriate inlet manifold 65 and outlet manifold 70 with each of the plasma plates and blood plates being separated by an appropriate membrane 75. As illustrated, the blood fractionator 25 is comprised of a stack 45 of five separate plates and four membranes 75 interleaved between the plates such that each plasma plate 50, 60 faces a blood plate 55 and is separated therefrom by an appropriate membrane 75. It will be appreciated that the stack 45 could as easily be comprised of a stack of plates in which the external plates are blood plates having two double sided plasma plates separated by an internal double sided blood plate. The number of plates also could be increased.

Referring now to the external plasma plates 50, it will be appreciated that although the plates are not identical, they are mirror images of one another for the sake of brevity like numbers have been placed on like portions of each end plate 50. As seen in FIG. 4 each external plasma plate 50 is an oval member 80 with an outer flat surface 81 opposed by an inner flat surface 82. The plate 50 is generally oval in shape and has a large inlet end 83 and a small outlet end 84. There are opposed recesses 85 in the side edges of the oval member 80 to provide for easy handling and a large notch 86 in the shall outlet end 84 having an end surface 86a and a small notch 87 in the large inlet end 83 having a flat end surface 87a.

Each of the end plasma plates 50 has on the inside flat surface 82 thereof a plasma collection channel 9 which has a trapezoidal portion 91 defined by side edges 92 and end edges 93. Toward the small outlet end 84 of the end plasma plate 50 is a transversely extending slot 94 in fluid communication with a plurality of longitudinally extending shallow collection grooves 95 separated by ridges 96. As hereinafter explained, the slot 94 is substantially deeper than the shallow collection grooves 95 and the portion of the grooves 95 adjacent the slot 94 are deeper than the remainder of the grooves 95 but shallower than the slot. A plasma outlet 98 in the form of an aperture extending from the end surface 86a extends through the oval member 80 and is in fluid communication with the slot 94. Finally, an oval tongue 99 surrounds the plasma collection channel 90, for a purpose hereinafter explained.

Referring now to FIGS. 6 and 11 through 14, there is illustrated a blood plate 55 which is provided with the same configuration on both sides thereof, whereby only one side will be described for the sake of brevity. Each of the blood plates 55 is identical in configuration and has in the opposed flat surfaces 102 thereof a blood flow channel 100, the plate 55 being generally oval in shape and identical in size to the external plasma plates 50 previously described. For that matter, all of the plates 50, 55 and 60 have the same general dimensions in plan view. The blood plate 55 has an edge surface 101 and opposed flat side surfaces 102, it being the surfaces 102 in which the blood flow channels 100 are positioned. The blood plate 55 has a large inlet end 103 and a small outlet end 104, with recesses 105 being provided in the side edges as previously discussed with respect to the end plasma plates 50. As in the end plasma plates 50, there is a large notch 106 in the small outlet end 104, the notch having a end surface 106a and there is a small notch 107 at the large inlet end 103, the small notch 107 being provided with an end surface 107a. A groove 109 extends around the periphery of both flat side surfaces 102 and each is complementary in shape to the tongue 99 in the adjacent end plasma plate 50 and are shaped and dimensioned to receive therein the associated tongue 99 as well as the thickness of the membrane 75, as will be explained. Although shown with grooves on blood plate 55 and tongues on plates 50, the tongues and grooves can be interchanged.

Each of the blood flow channels 100 has a distribution portion 110 and a collection portion 110a in the form of a multiple bifurcated manifolds, these distribution and collection portions are identical in shape but not in dimension, as will be explained, but for the case of brevity again, like numerals have been applied to like portions of the manifolds 110, 110a. Both the distribution portion 110 and the collection portion 110a, that is the bifurcated manifolds are in fluid communication with a transfer portion 160, all for a purpose hereinafter explained.

Referring now to the large inlet end 103 of the blood plate 55, there is an inlet aperture 112 extending through the end surface 107a of the notch 107 and extending longitudinally of the blood plate 55. The inlet 112 has a counterbore portion 113 at one end thereof and communicates with an aperture 114 which extends through the plate 55, as best seen in FIGS. 6 and 11, so as to provide communication between the inlet manifold 65 and the blood flow channel 100 on both sides of the plate 55. As noticed, the inside facing surface 114a of the aperture 114 is rounded at the juncture with the bifurcated manifold 110 to prevent contact of the blood flowing therethrough with a sharp edge for a purpose, as will hereinafter be set forth.

The manifolds 110 and 110a on each end of the blood plate 55 are multiple bifurcated manifolds in which each path is divided twice and there are five such divisions resulting in a single blood stream entering through inlet 112 being divided into 32 blood streams, as hereinafter set forth, at the delivery end of the manifold 110. Specifically, blood flowing through the aperture 114 enters the blood flow channel 100 at the main channel 115 and there is split at the first bifurcation into two channels 116 with the surfaces 117 being rounded or arcuate so as to prevent the impingement of the blood into corners which results in stagnation and less smooth distribution and flow. Each of the channels 116 curves as at 118 into a secondary channel 119 which is again bifurcated into channels 121, both the arcuate portions 122 and 123 being formed to prevent stagnation and increase smooth flow of blood through the manifold 110. From the channels 121 the blood into the tertiary channel 129 where it is again bifurcated into channels 131 and channels 131 are again provided with arcuate surfaces 132 and 133 for the same purposes as previously described. The blood flows from channels 131 into the fourth tier of channels 139 where they are again bifurcated into channels 141, the channels 141 being provided with smooth arcuate surfaces 142 and 143 to prevent stagnation of blood as it flows through the distribution portion of the blood flow channel 100. A fifth tier channel 149 receives the blood from the channels 141 and is bifurcated as at 151 into two additional streams, thereby making the five bifurcations previously described with each of the channels 151 having rounded or arcuate smooth surfaces 152 and 153 to prevent any stagnation of blood and to enhance the flow characteristics thereof. Each of the bifurcated channels 151 has an entrance 155 to the transfer portion 160 of the blood flow channel 100. As before indicated there are 32 entrances 155 to the transfer portion 160.

As best seen in FIG. 11, the bifurcated manifolds 110, 110a have a continuously changing depth with the manifolds being deeper at the inlet 112 or outlet 112a and being shallower at the junctures with the transfer portion 160 of the blood flow channel 100. It is preferred that this gradation in depth be uniform so that the depth of the manifolds 110, 110a will be the same along a plane transverse to the longitudinally established flow path through the plate 55. Preferably, the varying depth of the manifolds 110, 110a is such that the depth of the manifolds at the juncture with the transfer portion 160 is exactly the same as the depth of the transfer portion.

The transfer portion 160 is generally trapezoidal in plan view and is defined by side edges 161 and end edges 162 with a generally flat uniformly deep surface 163 which is shallow and as hereinbefore set forth of the same depth as the entrances 155 from both the collection and distribution portions of manifolds 110, 110a. Because the transfer portion 160 of the blood flow channel 100 is trapezoidal in shape, that is it tapers from the inlet end 103 to the outlet end 104 of the plate 55, the transverse dimension of the collection manifold 110a is less than the transverse dimension of the distribution manifold 110. However, the configuration of the collection manifold 110a is precisely the same as the configuration of the distribution manifold 110; therefore, like numerals have been placed on like portions to prevent repetitive description. Suffice it to say that the entrances 155 of the collection manifold 110a at the end of the transfer portion 160 are identical in configuration and number but smaller in overall transverse dimension than the entrances 155 from the manifold 110. The same five bifurcations are in the manifold 110a as in the manifold 110 and the vertically extending aperture 114 with the same arcuate surface 114a connects the outlet 112a to the collection manifold 110a, the outlet 112a being provided in the end edge 106a of the notch 106 and having a counterbore portion 113a of the same size and dimension as the counterbore 113 at the inlet end 103.

Similarly, the collection manifold 110a has a varying depth in the same manner as the distribution manifold 110, that is the depth of the entrances 155 is the same as the depth of the transfer portion 160 and the depth of the manifold increases uniformly from the entrances 155 toward the aperture 114. Again, the increase in depth is preferably uniform so that the depth of the manifold 110a would be exactly the same along a plane transverse to the longitudinally established blood flow path of the blood plate 155.

Accordingly, it is seen that the blood plate 55 has provided blood flow channels 100 on both sides thereof and each blood flow channel 100 is identical and has a distribution portion in the form of a multiple bifurcated manifold 110, a transfer portion 160 and a collection portion in the form of a multiple bifurcated manifold 110a. The blood flow is established longitudinally of the plate and flows from the inlet 112 through the end surface 107a of the notch 107 and exits through the outlet 112a through the end surface 106a of the notch 106 which is opposite to the notch 107.

The multiple bifurcations of the manifolds 110 and 110a are most easily seen in reference to FIGS. 12 and 14. FIG. 12 is taken along a portion of the manifold 110 where there are four channels 129 and FIG. 14 is taken along the entrances 155 of the manifold 110 wherein there are thirty-two channels. As seer therefore, the blood flow has been bifurcated five times so that from a single blood stream at the inlet 112 it is divided twice five times, there being two channels 116, four channels 121, eight channels 131, sixteen channels 141 and thirty-two channels 151 which terminate in the entrances 155. These five bifurcations repeated on the collection manifold 110a to combine, in a uniform manner, the thirty-two, streams entering the collection manifold 110a from the transfer portion 160 to a single outlet stream in the outlet 112a. FIG. 13 clearly illustrated the two transfer portions 160 of the blood flow channel 100 which consist of a shallow trapezoidal shaped groove, the trapezoidal shape being for a purpose hereinafter set forth.

Referring now to FIGS. 5, 7-10, there is shown the internal plasma plate 60 having the same configuration on both sides of the plate and more particularly the plate 60 has opposed flat surfaces 171 and a peripheral edge surface 172. There is a large end 173 which corresponds to the inlet 26 and a small end 174 which corresponds to the outlet 36. In the side of the edge surfaces 172 are two finger recesses 175 of the same size and dimension as the previously described recesses 85 and 105. At the outlet end 36 corresponding to the small end 174 is a large notch 176 of the same size and configuration as the previously described notches 86 and 106 respectively in the end plasma plates 50 and the blood plates 55. The large notch 176 has an end surface 176a. Opposite the large notch 176 is a smaller notch 177 in the inlet 26 of the device 25 which corresponds to the small end 173 of the plate 60. Notch 177 is of the same size and dimension as the previously described notches 87 and 107 and is provided with an end surface 177a. A tongue 179 extends around the periphery of each side surface 171 of the plate 60 and is constructed and arranged to fit within one of the notches 109 in the blood plates 55.

A plasma collection channel 180 is in both side surfaces 171 of the plate 60 and is of the same size and dimension and is similarly constructed to the plasma collection channel 90 in the end plasma plates 50. Specifically, the plasma collection channel 180 includes a slot 181 which extends entirely through the plate 60 and opens onto both opposed substantially flat surfaces 171. An aperture 182 forms the plasma outlet which extends through the surface 176a of the notch 176 and has a counterbore area 183 for receiving a suitable fixture from the tubing 42 which leads to the plasma collection receptacle or bag 40. It is noted that in plan view, the plasma outlet 182 is in vertical alignment with the plasma outlets 98 of the end plasma plates 50; however, in FIG. 5 the plasma plate 60 is reversed so that while it appears the plasma outlet 182 is displaced, it is seen, particularly from FIG. 4, that the plasma outlet 182 is aligned with each of the other plasma outlets 98 of the end plasma plates 50, for a purpose hereinafter described.

The plasma collection channel 180 further includes a trapezoidally shaped collection area 185 defined by side edges 186 and end edges 187, the trapezoidal plasma collection area being substantially the same size and dimension as the transfer portion 160 of the blood plates 55 and the same as the trapezoidal plasma collection portion or area 91 of the end plasma plates 50. As with the end plasma plates 50, there are a plurality of longitudinally extending shallow collection grooves 195 separated by ridges 196. Immediately adjacent the transversely extending slot 181 is a portion 197 of the grooves 195 which is deeper than the remainder of the grooves 195 but of course shallower than the slot 181 which extends entirely through the plate 60.

As seen, therefore, the blood fractionator 25 is comprised of a stack 45 of alternating blood plates 55 and plasma plates 50, 60 interleaved by membranes 75. The membrane 75 is selected so that the pore size of the membrane selectively passes the blood fraction to be collected. In the case of a plasma collection device, the membrane 75 preferably has a pore size in the range of from about 0.1 microns to about 1.5 microns. Membranes are commercially available with pore sizes 0.6 microns, 0.65 microns and 1.0 microns. Others may be available. Nuclepore, Gelman, Millipore and Sartorius produce membranes suitable for blood plasma harvesting. Other blood fractions which are of interest and which may be separated by the fractionator 25 are protein-free filtrates and protein fractions and membranes useful for these purposes would necessarily have pore sizes in the range of from about 50 Angstrom to about 0.05 microns. These membranes, also are readily available as will be appreciated by those skilled in the art.

The stack 45 is sealed in part and clearly aligned by the tongue and groove mechanism previously described. For instance, the end plasma plates 50 have the tongues 99 while the blood plates 55 are provided with the grooves 109 and the central plasma plate 60 has the tongues 179, all of which are shaped, constructed and arranged to fit one within the other while accommodating therein membrane 75 which, as illustrated in FIGS. 15-18, extends from edge to edge of the various plates. The usefulness of the tongue and groove construction is that the membranes 75 remain imperforate which is critical to the design of the blood fractionator 25 and to the operation of the system 20 since membrane rupture or leakage can result in serious problems Furthermore, an imperforate membrane effectively constructs blood flow channels without the need for gaskets or other fluid separating components. In any event, utmost care is taken to ensure the leak free nature of the membranes 75 and to this end, the design of a device which provides an imperforate membrane 75 is a significant advantage.

Completing the blood fractionator 25 and coacting with the stack 45 are the blood inlet manifold 65 and the blood and plasma outlet manifold 70. The function of the blood inlet manifold is extremely important and is to uniformly distribute the blood from the donor 30 which enters the blood fractionator 25 through the inlet 26 and particularly through the tube 27 among the blood plates 55. In the preferred embodiment, there are two blood plates 55, whereby the function of the blood inlet manifold 65 is to uniformly distribute the blood flow from the donor 30 evenly between the two blood plates 55 and specifically to the respective inlets 112 of each plate leading to the associated multiple bifurcated manifolds 110. The blood inlet manifold 65 is received in the aligned series of notches 87, 107 and 177 and, as best seen in FIG. 19, the blood inlet manifold is comprised of a solid block, preferably of plastic 210, having a blood inlet port 211, a bifurcated passageway 213 and two fittings 214 of a size and dimension to fit snugly within the counterbore portion 113 of each blood plate 55.

Referring now to the blood and plasma outlet manifold 70 illustrated particularly in FIGS. 4, 15 and 17, there is a block, preferably of plastic 200 which has a blood outlet port 201 connected to the tubing 37 so that blood flowing from the blood fractionator 25 in the direction of the arrow 38 returns to the donor 30. The blood outlet port 201 is in fluid communication with a bifurcated passageway 203 which leads to two fittings 204 constructed and arranged to fit within the counterbore portions 113a of the two blood plates 55. The block 200 like the block 210 is constructed and arranged snugly to fit within the appropriate opening formed by the series of notches 86, 106 and 76 of the stack 45 of plates. The outlet manifold 70 also has a plasma outlet port 202 connected to the tubing 42 which permits plasma to flow in the direction of the arrow 43 into the plasma collection receptacle or bag 40.

The plasma outlet port 202 is connected to a trifurcated passageway 206 which has connected thereto two end fittings 207 and a center fitting 208 respectively fitting into the counterbore portions of the plasma end plate outlets 98 and the counterbore portion 183 of the interior plasma plate 60. The fit of the inlet manifold 65 and the outlet manifold 70 is such as to provide a fluid tight fit between the manifold and the appropriate portions of each plate, thereby to ensure no leaks during operation. It will be appreciated that the plates are maintained in their stacked configuration by the two manifolds 65 and 70 which may fixedly secured to their respective series of notches by a suitable adhesive which is biocompatible with blood and blood components or by ultrasonic welding or other method well known in the art.

In the plasma harvesting art, there has been a long felt need to provide an easier, safer, more economical method of harvesting plasma than that which is commercially available. There has been a significant amount of money both from the private sector and from the government dedicated to finding solutions to the problem, but as of yet there has been no satisfactory solution. Problems encountered in the art are many but the most significant problem is the rapid degradation in plasma production with time for any device heretofore discovered or proposed. It is not unusual to have initial plasma production that is significant and commercially acceptable however within a relatively short time, in the order of less than a half hour, plasma production falls off so dramatically that as of the present date no commercial device is available which meets the criteria heretofore set forth.

The present blood fractionator 25 and system 20 meet all the criteria set forth above and provides commercially acceptable plasma collection rates even after more than one half hour of continuous plasma production. When harvesting blood with a 5-plate embodiment, it is preferable that the blood flow rate from the donor 30 to the blood fractionator 25 be in the range of from about 50 milliliters per minute to about 100 milliliters per minute. Blood flow rates above 100 milliliters per minute do not significantly augment plasma flow unless additional plates are added, whereas flow rates less than about 50 milliliters per minute result in low plasma production. Clearly, blood hematocrit affects the amount of plasma produced with higher hematocrit values producing less plasma due to lower filtration rate.

In human donors it is usual to encounter hematocrit values in the range of from about 38 to about 55 percent. The taper of the plates in the stack 45 has been calculated on the basis on a average hematocrit value of about 45 percent and is also determined, to some extent, by the length of the blood flow path and particularly by the length of the trapezoidal area of the various plates. The taper is used to maintain constant the blood flow rate as plasma transfers through the membrane 75 thereby decreasing the volume of the blood. It is also important to maintain shear constant and the taper also accomplishes this purpose. In the blood fractionator 25 described, the calculated blood flow velocity which was maintained substantially constant due to the construction of the device was about 5.7 centimeters per second with a mean shear of 6027 sec$^{-1}$.

In addition to the tapered blood channel to maintain constant velocity and shear, it was also discovered that in order to obtain commercially acceptable plasma collection rates over a substantial period of time, it was beneficial to provide entry acceleration of the blood from the manifold to each plate and this, of course, is provided by the inlet manifold 65. An additional important feature of the fractionator 25 is the progressive decrease in the bifurcated manifold channel depth from entry to exit, this referring to the bifurcated manifolds 110 in each of the blood plates 55.

Still another important feature of the blood fractionator 25 is the shallow parallel grooves 195 in the plasma plate 60 and the similar grooves 95 in the end plates 50 which function to optimize transmembrane pressure and to minimize flow resistance to plasma during operation of the fractionator 25. The optimization of the transmembrane pressure greatly reduces the rate at which red blood cells plug the pores of the membrane 75.

Still another important feature of the system 20 and the fractionator 25 is the vertical inlet manifold 65 and outlet manifold 70 which, in cooperation with other design features of the fractionator, result in a uniform blood distribution intraplate and a uniform blood distribution along each blood flow channel 100. Another aspect of the inlet manifold 65 and the outlet manifold 70 which cooperates with tongue and groove construction of the fractionator 25 is the elegant seal of the device 25 which simplifies the internal gasketing necessary to maintain a liquid tight seal for the fractionator 25.

In a constructional example of the fractionator 25, each of the plates 50, 55 and 60 is 0.19 inches thick. The width at the section 12—12 is 3.0 inches, the width at section 13—13 is about 3.04 inches and the width at section 14—14 is about 2.85 inches. The overall length of the fractionator, absent the inlet 211 and the outlet 201 is about 4.89 inches and the overall width at its widest part is about 3.38 inches. The dimension of the blood transfer portion 160 of the blood transfer plate 55 is about 3.0 inches at its widest and about 2.2 inches and its narrowest, this representing a taper in the order of about 8°.

It should be understood that the taper is calculated on the basis that plasma transfer through the membrane 75 is uniform throughout the blood transfer portion 160 and on the length of the portion 160. For longer devices, the taper is necessarily greater and tapers of up to about 10° are contemplated. The length of the blood transfer area 160 is about 2.6 inches.

The passageway 114 which connects the inlets 112 with the multiple bifurcated manifold 110 has a diameter of about 0.125" and the entrances 155 are each about 0.031" wide and are spaced about 0.093", center to center at the large end and 0.069" center to center at the small end.

Referring now to the plasma plates and particularly to FIGS. 9 and 10 the depth of the longitudinally extending shallow grooves 195, and for that matter the grooves 95, are preferably about 3 mils. Each of the grooves 95, 195 as best seen in FIG. 10, are described by an arc 62 mils in radius and each of the ridges 96, 196 are about 46 mils center to center. The depth of the portions 197 of the grooves 195 and the portions of the grooves 95 unnumbered immediately adjacent the respective slots, 94, 181, have a depth of about 0.052". This portion of the grooves is important because it decreases flow resistance as the plasma or blood fraction flows into the slots. Preferably, for grooves 95, 195, 3 mils deep, the portion 197 would be in the range of from about 0.04" to about 0.07". Less than about 0.04" would not accomplish the required reduction in blood fraction or plasma flow resistance while greater than about 0.07" would enhance clogging by red cells.

Another feature of the blood fractionator 25 is the continuously decreasing depth of the multiple bifurcated manifolds 110, 110a from the inlet 112, outlet 112a to the blood transfer area 160. This is important because blood exits the multiple bifurcated manifold 110 and particularly the entrances 155 with a slight inclination toward the surface of the adjacent membrane 75 which seems to be an advantage to the present design. Because relatively high shear is important to prevent the membrane 75 from clogging with red blood cells, the blood flow channel was kept shallow. As channel height was increased, filtration rate decreased.

Summarizing, there are a number of factors which apparently cooperate to enable a commercial device to be made which operates satisfactorily and which meets all the objects of the present invention. Of the most important features of the present invention are the uniform intraplate distribution of blood by the inlet manifold 65, the uniform transverse distribution of blood across the plates by the multiple bifurcated manifolds 110, the uniform flow velocity and shear accomplished by means of the tapered transfer areas 160, the shallow blood flow path accomplished by the depth of the transfer areas 160 and the immediately adjacent membrane 75, the optimization of transmembrane pressure by the shallow grooves 95, 195 of the plasma plates 50, 60, the reduction in the flow resistance of the plasma due to the increased depth of the grooves 195 at the portions 197 and the like portions on the end plasma plates 50, the uniform collection of the plasma by the outlet manifold 70, and the uniform condensation of the multiple streams into a single outlet stream by the multiple bifurcated manifold 110a at the outlet end 36 of the fractionator 25 and the use of a design which obviates the necessity for internal gaskets or perforations of the membrane.

Reported hereafter in Tables I, II and III are data obtained with in vitro experiments with human blood. Because of the nature of stored human blood, the hematocrit value was adjusted to 33 percent with saline. In Tables I and III, a single membrane device was used and hence the blood flow rate was 20 milliliters per minute whereas Table II reports a five layer, four channel device wherein the total blood flow rate was 80 milliliters per minute. Several different design modifications are shown. Accordingly, in order to extrapolate the initial and final filtrate rates reported in Tables I and III, these values must be multiplied by four.

blood used in the experiments reported in Tables I–III.

TABLE IV

Dog experiments with B00191/P00181
Blood pumped from femoral artery and returned to femoral vein.
Citrate pumped into entry blood line prior to entry into device.

| Blood Channel Height-In. | Membrane | Dog | Blood Flow ml/min | Citrate Flow ml/min | Total Flow ml/min | Average Plasma Flow ml/min | Initial Plasma Flow | Final Plasma Flow |
|---|---|---|---|---|---|---|---|---|
| .003 | Nuclepore 0.6 u | 1 | 58 | 22 | 80 | 21.3 | 22.5 | 18.0 |
| .003 | Nuclepore 0.6 u | 1 | 58 | 22 | 80 | 19.3 | 20.5 | 17.0 |
| .003 | Nuclepore 0.6 u | 1 | 58 | 22 | 80 | 17.9 | 18.5 | 17.5 |
| .003 | Nucleport 0.6 u | 2 | 58 | 22 | 80 | 22.6 | 24.0 | 22.0 |
| .0045 | Gelman | 2 | 58 | 22 | 80 | 16.9 | 17.5 | 17.0 |
| .003 | Gelman | 2 | 58 | 22 | 80 | 30.8 | 35.0 | 28.0 |
| .003 | Gelman | 3 | 70 | 10 | 80 | 21.6 | 25.5 | 17.0 |
| .003 | Gelman | 3 | 70 | 10 | 80 | 21.1 | 24.5 | 19.0 |
| .0045 | Gelman | 3 | 70 | 10 | 80 | 11.1 | 11.5 | 10.5 |
| .003 | Gelman | 3 | 58 | 22 | 80 | 25.3 | 28.0 | 24.0 |
| .003 | Nucleport .65 u | 3 | 58 | 22 | 80 | 21.9 | 25.0 | 20.5 |

TABLES I, II AND III

TABLE I

B00191/P00181 Results
All experiments in vitro with human blood, hematocrit adjusted to 33 percent with saline.
Pump speed = 20 ml/minute

| Number Experiments | Membrane | Inlet Pressure mm Hg | Outlet Pressure mm Hg | Initial Filtrate ml/min | Final Filtrate ml/min |
|---|---|---|---|---|---|
| 7 | Nuclepore 0.6 u | 244 | 25 | 6.2 | 4.3 |
| 6 | Nuclepore 1.0 u | 275 | — | 7.5 | 6.8 |
| 4 | Gelman 0.65 u | 404 | — | 8.2 | 6.8 |

TABLE II

B00191/P00181 Results
All experiments in vitro per Table I.
Pump speed = 80 ml/min.
Five layers with 4 blood channels in parallel.

| Number Experiments | Membrane | Inlet Pressure mm Hg | Outlet Pressure mm Hg | Initial Filtrate ml/min | Final Filtrate ml/min |
|---|---|---|---|---|---|
| 8 | Nuclepore 0.6 u | 215 | — | 26.1 | 12.9 |
| 1 | Nuclepore 1.0 u | 96 | — | 20.5 | 15.5 |
| 12 | Gelman 0.65 u | 239 | — | 25.0 | 20.9 |

TABLE III

B00198/P00188 Results
All experiments in vitro per Table I.
Pump speed = 20 ml/min. Single layer.

| Experiments | Membrane | Inlet Pressure mm Hg | Outlet Pressure mm Hg | Initial Filtrate ml/min | Final Filtrate ml/min |
|---|---|---|---|---|---|
| 6 | Nuclepore 0.6 u | 154 | — | 4.6 | 3.1 |
| 2 | Nuclepore 1.0 u | 189 | — | 7.3 | 6.5 |
| 4 | Gelman 0.65 u | 190 | — | 4.4 | 2.1 |

Table IV reports the results of various dog experiments, it being noted that fresh blood produced a significantly high final plasma flow rate than did the stored blood used in the experiments reported in Tables I–III.

Table IV also illustrates certain results with blood flow channels having depths of 3 mils and 4.5 mils, but as seen from the data significant differences were not seen. For a single membrane device of the type reported in Tables I–III, typical manifold entrance velocities at 114 were 4.2 centimeters per second and typical manifold exit velocities at 155 were 17.4 centimeters per second. The blood flow channel velocity was, as previously reported, 5.7 centimeters per second and the blood channel mean shear was 6.027 sec The manifold 110 flow channels, at the inlet were approximately 125 mils deep with the depth decreasing progressively, and uniformly, to 3 mils at the juncture between the ends of the manifolds 110 and the beginnings of the blood transfer area 160 on the one hand and the entrance to the manifold and the end of the blood transfer area on the other hand.

In the blood fractionator 25 as illustrated, there are five plates with four blood-fraction plate pairs separated by four sheets of membrane. It is clear that larger or smaller stacks may be used without departing from the scope of the invention.

As illustrated, the system 20 is useful to provide a method of continuously fractionating blood in situ, that is continuously fractionating blood utilizing a closed loop system with a donor 30. The closed loop consists of the tubes 27 and 37 in combination with the double lumen needle, needles or catheter 28 and the blood fractionator 25 enabling a method to be used in which blood is continuously pumped via the pump from the donor 30 in a closed loop through the blood fractionator 25 and returned to the donor. The blood fraction is continuously produced during the operation of the method and is collected in the receptacle or blood fraction bag 40. The method optimizes transmembrane pressure resulting in continued satisfactory blood fraction collection rates for prolonged durations. The method also includes the use of an anti-coagulant 35 which may be citrated saline or heparinized saline, or other well known anti-coagulants. The flow rate of the anti-coagulant and the blood are fixed by the pumps 31 and 31A used in conjunction with the supply 35 of anti-coagulant A flow rate of 65 milliliters of blood per minute and 15 milliliters of anti-coagulant per minute for a total inlet flow rate to the fractionator 25 of about 80 milliliters per minute has been satisfactory.

By the design of the fractionator 25, the blood velocity is maintained constant through the transfer area of each plate, but the blood velocity is accelerated from manifold inlet to manifold outlet. In addition, the blood shear is also maintained substantially constant from manifold inlet to manifold outlet.

The system 20 of the present invention, as previously described, may have other safety features not illustrated. For instance, an air bubble detection device may be included on the return tubing 37 and there may be a blood leak detector or other such equipment elsewhere located in the system, all well within the skill of the art. An important and unique feature of the blood fractionator 25 is the minimum volume of the device. All of the blood channels of the device 25, including both end manifolds 110, 110a, have a volume less than 2.5 ml. Volume of the plasma compartments, including manifolds, is less than 2 ml. This feature, not present in previously described devices, minimizes blood loss by the donor and maximizes plasma recovery The minimal amounts of plasma left in the device 25 are important to commercial utilization of the device. Accordingly, low blood and plasma retention volumes of less than 10 mls is an important commercial feature of the invention. Total blood volume of the tubing plus fractionator 25 is estimated to be less than 20 ml.

Total membrane area of the device is 176 $cm^2$ whereas previously described devices may use as much as 10,000 $cm^2$ of membrane. The reduction of membrane area contributes significantly to reduction of costs. This is a substantial improvement over prior art devices which require larger quantities of membrane, thereby resulting in a substantially more expensive device, not suitable for a disposable device.

While there has been described what at present is considered to be the preferred embodiment of the present invention, it will be understood that various modifications and alterations may be made therein without departing from the true scope and spirit of the present invention which is intended to be covered in the claims appended hereto.

What is claimed is:

1. A device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof, said transfer portion of said blood flow channel being more narrow at the outlet thereof than at the inlet thereof sufficiently to maintain blood velocity substantially constant through said transfer portion, each plasma collection channel being substantially in registry with said transfer portion of said facing blood flow channel for receiving plasma passing through said membrane, and a plasma outlet for conducting plasma from each plasma collection channel, whereby plasma continuously transfers from blood passing through said transfer portion of each blood flow channel through the membrane to the adjacent plasma collection channel to said plasma outlet.

2. The device of claim 1, wherein each plate in said stack of plates if flat.

3. The device of claim 1, wherein each plate has either a blood flow channel or a plasma collection channel therein.

4. The device of claim 1, wherein the two outside plates in said stack of plates each have a plasma collection channel on the inside facing surface thereof.

5. The device of claim 1, wherein at least one blood plate has a blood flow channel in each of the opposite surfaces thereof.

6. The device of claim 1, wherein at least one plasma plate has a plasma collection channel in each of the opposite surfaces thereof.

7. The device of claim 1, wherein there are five plates in said stack with at least one plate having a blood flow channel in opposite surfaces thereof and one plasma plate having a plasma collection channel in opposite surfaces thereof.

8. The device of claim 1, wherein said transfer portion of said blood flow channel is shallow having a depth in the range of from about 1 mil to about 10 mils.

9. The device of claim 8, wherein the depth of the transfer portion is about 3 mils.

10. The device of claim 1, wherein each plasma collection channel has substantially the same depth as said transfer portion of each blood collection channel.

11. The device of claim 10, wherein a plasma collection channel has a transversely extending slot at one end thereof deeper than the remaining portion of the plasma collection channel.

12. A device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof tapered from inlet to outlet to maintain the blood flow velocity and shear substantially constant as plasma is transferred from the blood, each plasma collection channel being tapered and substantially in registry with said tapered transfer portion of said facing blood flow channel for receiving plasma passing through said membrane, and a plasma outlet for conducting plasma from each plasma collection channel, whereby plasma continuously transfers from blood passing through said transfer portion of each blood flow channel through the membrane to the adjacent plasma collection channel to said plasma outlet.

13. The device of claim 12, wherein said transfer portion of said blood flow channel is trapezoidal in plan view.

14. The device of claim 13, wherein the depth of the transfer portion of said blood flow channel is less than 10 mils.

15. The device of claim 13, wherein the angle of the taper from the inlet to the outlet of said transfer portion is in the range of from about 5° to about 10°.

16. The device of claim 13, wherein the angle of said taper is between about 8°.

17. The device of claim 12, wherein said plasma collection groove has substantially the same depth as the depth of the transfer portion of said blood flow channel.

18. A device for continuously producing plasma, comprising a stack of at least two plates having at least one surface with a blood flow channel therein facing a surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof, said transfer portion of said blood flow channel being more narrow at the outlet thereof than at the inlet thereto sufficiently to maintain blood velocity substantially constant through said transfer portion, each plasma collection channel being substantially in registry with said transfer portion of said facing blood flow channel for receiving plasma passing through said membrane, means associated with each plasma collection channel for minimizing transmembrane pressure to reduce the rate at which red blood cells plug said membrane, and a plasma outlet for conducting plasma from each plasma collection channel, whereby plasma continuously transfers from blood passing in said transfer portion of each blood flow channel through the membrane to the adjacent plasma collection channel to said plasma outlet.

19. The device of claim 18, wherein said plasma collection channel is of substantially the same shape and dimension as said transfer portion of said blood flow channel and has a plurality of longitudinally extending grooves therein, said grooves having a depth in the range of from about 1 mil to about 10 mils.

20. The device of claim 19, wherein the depth of said grooves is in the range of from about 3 mils to about 5 mils.

21. The device of claim 18, wherein said grooves are about 3 mils deep, are transversely spaced apart about 45 mils center-to-center and are separated by ridges about 15 mils wide.

22. The device of claim 19, and further comprising a slot at the end of said grooves connected to same, said slot being deeper than the depth of said longitudinally extending groove.

23. The device of claim 22, wherein the portion of each groove immediately adjacent said slot is deeper than the remainder of said grooves to reduce plasma flow resistance prior to entry of plasma into said slot.

24. A device for continuously producing plasma, comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet extending through the end surface of each plate having a blood flow channel therein for conducting blood to said blood flow channel and an outlet extending through the end surface of said plate for conducting blood therefrom to establish a longitudinally extending blood flow path, each of said blood flow channels having a distribution portion for uniformly distributing blood transversely of the blood flow path and a transfer portion extending longitudinally thereof, said transfer portion of said blood flow channel being more narrow at the outlet thereof than at the inlet thereto sufficiently to maintain blood velocity substantially constant through said transfer portion, each of said plasma collection channels being substantially in registry with said transfer portion of said facing blood flow channel for receiving plasma passing through said membrane, and a plasma outlet for conducting plasma from each of said plasma collection channels, whereby plasma continuously transfers from blood passing through said transfer portion of each blood flow channel through the membrane to the adjacent plasma collection channel to said plasma outlet.

25. The device of claim 24, wherein said inlet is in the middle of said end surface.

26. The device of claim 25, wherein said inlet and outlet are longitudinally aligned.

27. The device of claim 24, wherein an aperture extends generally perpendicularly to the surface having said blood flow channel therein connecting said inlet and said blood flow channel.

28. The device of claim 27, wherein the juncture between said aperture extending generally perpendicularly from said inlet to said blood flow channel is arcuate to provide a smooth flow surface for blood flowing through said inlet to said blood flow channel.

29. The device of claim 24, and further comprising an outlet extending through the end surface of each plate having a plasma collection channel therein.

30. The device of claim 29, and further comprising a slot extending transversely to said collection channel in fluid communication therewith having a depth exceeding that of the plasma collection channel, said slot being connected to said outlet.

31. A device for continuously producing plasma, comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet for conducting blood to each blood flow channel and an outlet for conducting blood therefrom to establish a longitudinally extending blood flow path, each of said blood flow channels having a distribution portion for uniformly distributing blood transversely of the blood flow path inlet and a transfer portion extending longitudinally thereof and a combining portion for conducting blood from said transfer portion to said outlet, said transfer portion of said blood flow channel being more narrow at the outlet thereof than at the inlet thereto sufficiently to maintain blood velocity substantially constant through said transfer portion, said distribution and said combining portions each comprising a multiple bifurcated manifold wherein the depth of the manifold increases from said transfer portion to said inlet or said outlet, each of said plasma collection channels being substantially in registry with said transfer portion of said facing blood flow channel for receiving plasma passing through said membrane, and a plasma outlet for conducting plasma from each of said plasma collection channels, whereby plasma continuously transfers from blood passing through said transfer portion of each blood flow channel through the membrane to the adjacent plasma collection channel to said plasma outlet.

32. The device of claim 31, wherein there are five bifurcations in each of said distribution and combining portions thereby providing 32 blood streams entering said transfer portion and 32 entrances for said combining portion.

33. The device of claim 31, wherein said transfer portion of said blood flow channel has a depth in the range of between about 1 and 10 mils.

34. The device of claim 33, wherein the depth of said manifolds equals the depth of the transfer portion where the distribution and combining portions meet the transfer portion of each blood flow channel.

35. The device of claim 34, wherein the depth of said transfer portion is about 3 mils and the depth of said manifolds increases from about 3 mils at the juncture of the manifolds and the transfer portion to about 125 mils at the outlet and the inlet.

36. The device of claim 31, wherein the depth of the manifold increases substantially uniformly from said transfer portion to said inlet or said outlet.

37. The device of claim 31, wherein each branch of said bifurcated manifold has arcuate surfaces at each change in direction of blood flow thereby to improve blood flow through said manifold.

38. A device for continuously producing plasma, comprising a stack of at least two plates having at least one substantially flat surface with a blood flow channel therein facing a substantially flat surface with a plasma collection channel therein separated by a semipermeable membrane having a pore size in the range of from about 0.1 microns to about 1.5 microns, an inlet extending through the end surface of each plate having a blood flow channel therein for conducting blood to said blood flow channel and an outlet extending through the end surface of said plate for conducting blood therefrom to establish a longitudinally extending blood flow path, each of said blood flow channels having a distribution portion for uniformly distributing blood transversely of the blood flow path and a transfer portion extending longitudinally thereof and a combining portion for conducting blood from said transfer portion to said outlet, said transfer portion of said blood flow channel being more narrow at the outlet thereof than at the inlet thereto sufficiently to maintain blood velocity substantially constant through said transfer portion, said distribution and said combining portions each comprising a multiple bifurcated manifold wherein the depth of the manifold increases from said transfer portion to said inlet or said outlet, each plasma collection channel being substantially in registry with said transfer portion of said facing blood flow channel for receiving plasma passing through said membrane and a slot in communication with said plasma collection channel extending transversely thereof, and a plasma outlet in communication with said slots for conducting plasma from said plasma collection channels, whereby plasma continuously transfers from blood passing through said transfer portion of each blood flow channel through the membrane to the adjacent plasma collection channel to said plasma outlet.

39. The device of claim 38, wherein an aperture extends substantially perpendicularly to the surface having said blood flow channels therein connecting said inlet and said blood flow channel.

40. The device of claim 38, wherein the juncture between said aperture extending perpendicularly from said inlet to said blood flow channel is arcuate to provide a smooth flow surface for blood flowing through said inlet to said blood flow channel.

41. The device of claim 38, wherein there are five bifurcations in said distribution and combining portions thereby providing 32 blood streams entering said transfer portion and 32 entrances for said combining portion.

42. The device of claim 38, wherein each branch of said bifurcated manifold has arcuate surfaces at each change in direction of blood flow thereby to improve blood flow through said manifold.

43. The device of claim 38, wherein said transfer portion has a uniform depth in the range of from about 1 to about 10 mils, the depth of each manifold at the juncture with said transfer portion being the same as the depth of the transfer portion and the depth of said manifolds at the inlet and outlet being substantially greater.

44. A device for continuously producing plasma, comprising a stack of plates having a plurality of substantially flat surfaces with some of the surface having a blood flow channel therein and the others having a plasma collection channel therein, the facing surfaces in said stack having therein a blood flow channel and a plasma collection channel separated by a semipermeable membrane having a pore size in the range of from about 0.1 microns to about 1.5 microns, a blood inlet extending through the end surface of each plate having a blood flow channel therein for conducting blood to said blood flow channel and a blood outlet extending through the opposite end surface of said plate for conducting blood therefrom to establish a longitudinally extending blood flow path, each of said blood flow channels having a distribution portion for uniformly distributing blood transversely of the blood flow path and a transfer portion extending longitudinally thereof, said transfer portion of said blood flow channel being more narrow at the outlet thereof than at the inlet thereto sufficiently to maintain blood velocity substantially constant through said transfer portion, a blood inlet manifold connected to each blood inlet for distributing blood from a source thereof evenly among said blood inlets and a blood outlet manifold connected to each blood outlet for collecting blood therefrom and combining same into a single stream, each of said plasma collection channels being substantially in registry with said transfer portion of said facing blood flow channel for receiving plasma passing through said membrane, a plasma outlet extending through the end surface of each plasma having a plasma collection channel therein for conducting plasma therefrom, and a plasma outlet manifold connected to each plasma outlet for collecting plasma therefrom and combining same into a single stream, whereby plasma continuously transfers from blood passing through said transfer portion of each blood flow channel through the membrane to the adjacent plasma collection channel to said plasma outlet.

45. The device of claim 44, wherein said stack of plates contains two plates having blood flow channels in both surfaces thereof, said blood inlet manifold having a single bifurcated channel to divide a single blood stream into two blood streams of equal proportion and said blood outlet manifold has a single bifurcated channel to receive two blood streams and combine same into one blood stream.

46. The device of claim 44, wherein said stack of plates has three plates having a plasma collection channel therein, said plasma outlet manifold being constructed and arranged to combine three plasma streams into a single stream.

47. A device for continuously producing plasma, comprising a stack of interleaved blood plates and plasma plates with each blood plate having a blood flow channel in at least one substantially flat surface thereof and with each plasma plate having a plasma collection channel in at least one substantially flat surface thereof, said stack being constructed and arranged such that each surface having therein a blood flow channel faces a surface having therein a plasma collection channel separated by a semipermeable membrane having a pore size in the range of from about 0.1 microns to about 1.5 microns, a blood inlet extending through the end surface of each blood plate for conducting blood to said blood flow channel and a blood outlet extending through the opposite end surface of said plate for conducting blood therefrom to establish a longitudinally extending blood flow path, each of said blood flow channels having a distribution portion for uniformly distributing blood transversely of the blood flow path and a transfer portion extending longitudinally thereof tapered from inlet to outlet to maintain the blood flow velocity and shear substantially constant as plasma is transferred from the blood and a combining portion for conducting blood from said transfer portion to said outlet, said distribution and said combining portions each comprising a multiple bifurcated manifold wherein the depth of the manifold increases from said transfer portion to said inlet or said outlet, a blood inlet manifold connected to said stack and to each blood inlet for distributing blood from a source thereof substantially uniformly among said blood inlets and a blood outlet manifold connected to said stack and to each blood outlet for collecting blood therefrom and combining same into a single stream, each of said plasma collection channels being tapered and substantially in registry with said tapered transfer portion of said facing blood flow channel for receiving plasma passing through said membrane, and each of said plasma collection channels including a plurality of longitudinally extending grooves having a depth of about 3 mils terminating in a transversely extending collection slot, a plasma outlet for conducting plasma from each of said plasma collection slots, and a plasma outlet manifold connected to said stack and to each plasma outlet for collecting plasma therefrom and combining same into a single stream, whereby plasma continuously transfers from blood passing through said transfer portion of each blood flow channel through the membrane to the adjacent plasma collection channel to said plasma outlet.

48. The device of claim 47, wherein the two outside plates in said stack of plates are plasma plates having a plasma collection channel on the internally facing surface thereof.

49. The device of claim 48, wherein said stack of plates has five plates with two plates having blood flow channels in both surfaces thereof separated by a plate having a plasma collection channel in both surfaces thereof thereby to form a stack with two plasma plates as the outside plates each having one plasma collection channel on the inside facing surface thereof facing a blood plate having blood channels on the surfaces thereof and a plasma plate having plasma collection channels on both surfaces thereof between said blood plates.

50. The device of claim 49, wherein said membrane has a pore size in the range of from about 0.5 microns to about 1.5 microns.

51. The device of claim 47, and further comprising an aperture extending through each blood plate connecting the inlet to each blood flow channel and connecting said outlet to each blood flow channel.

52. The device of claim 47, wherein one plate in said stack of plates has a plasma collection channel in both surfaces thereof and said slot extends entirely through said plate to provide communication between said plasma collection channels.

53. A plate forming a blood flow path from one end to the other comprising, a pair of substantially flat opposed surfaces with at least one surface having a blood flow channel therein, and an inlet for conducting blood to said blood flow channel and an outlet for conducting blood therefrom to establish a longitudinally extending blood flow path, said blood flow channel having a distribution portion for uniformly distributing blood transversely of the blood flow path and a transfer portion extending longitudinally thereof tapered from inlet to outlet.

54. The plate of claim 53, wherein said transfer portion of said blood flow channel is trapezoidal in plan view.

55. The plate of claim 53, wherein the depth of the transfer portion of said blood flow channel is less than 10 mils.

56. The plate of claim 53, wherein the angle of the taper from the inlet to the outlet of said transfer portion is in the range of from about 5° to about 10°.

57. The plate of claim 53, wherein the angle of said taper is between about 8°.

58. The plate of claim 53, wherein both surfaces of said plate have a blood flow channel therein.

59. The plate of claim 53 and further comprising a semipermeable membrane having a pore size in the range of from about 0.1 microns to about 1.5 microns in contact with a portion of each surface having a blood flow channel therein.

60. A plate forming a blood flow path from on end to the other comprising, a pair of substantially flat opposed surfaces with at least one surface having a blood flow channel therein, and an inlet extending through the end surface of said plate for conducting blood to said blood flow channel and an outlet extending through the opposite end surface of said plate for conducting blood therefrom to establish a longitudinally extending blood flow path, said blood flow channel having a distribution portion for uniformly distributing blood transversely of the blood flow path and a transfer portion extending longitudinally thereof tapered from inlet to outlet.

61. The plate of claim 60, wherein said inlet is in the middle of said end surface.

62. The plate of claim 60, wherein said inlet and outlet are longitudinally aligned.

63. The plate of claim 60, wherein an aperture extends substantially perpendicularly to the surface having said blood flow channel therein connecting said inlet and said blood flow channel.

64. The plate of claim 60, wherein the juncture between said aperture extending perpendicularly from said inlet to said blood flow channel is curved to provide a smooth surface for blood flowing through said inlet to said blood flow channel.

65. The plate of claim 60 and further comprising a semipermeable membrane having a pore size in the range of from about 0.1 microns to about 1.5 microns in contact with a portion of each surface having a blood flow channel therein.

66. A plate forming a blood flow path from one end to the other comprising, a pair of substantially flat opposed surfaces with at least one surface having a blood flow channel therein, and an inlet extending through the end surface of said plate for conducting blood to said blood flow channel and an outlet extending through the opposite end surface of said plate for conducting blood therefrom to establish a longitudinally extending blood flow path, said blood flow channel having a distribution portion for uniformly distributing blood transversely of the blood flow path and a transfer portion extending longitudinally thereof tapered from inlet to outlet and a combining portion for conducting blood from said transfer portion to said outlet, said distribution and said combining portions each comprising a multiple bifurcated manifold wherein the depth of the manifold increases from said transfer portion to said inlet or said outlet.

67. The plate of claim 66, wherein there are five bifurcations in said distribution and combining portions thereby providing 32 blood streams entering said transfer portion and 32 entrances for said combining portion.

68. The plate of claim 67, wherein said transfer portion of said blood flow channel has a depth in the range of between about 1 and about 10 mils.

69. The plate of claim 66, wherein the depth of said manifolds equals the depth of said transfer portion where said distribution and combining portions meet said transfer portion of each blood flow channel.

70. The plate of claim 66, wherein the depth of said transfer portion is 3 mils and the depth of said manifolds increases from 3 mils at the juncture of said manifolds and said transfer portion to about 125 mils at said outlet and said inlet.

71. The plate of claim 66, wherein the depth of the manifold increases substantially uniformly from said transfer portion to said inlet or said outlet.

72. The plate of claim 66, wherein each branch of said bifurcated manifold has arcuate surfaces at each change in direction of blood flow thereby to improve blood flow through said manifold.

73. The plate of claim 66 and further comprising a semipermeable membrane having a pore size in the range of from about 0.1 microns to about 1.5 microns in contact with a portion of each surface having a blood flow channel therein.

74. A device for continuously producing a blood fraction, comprising a stack of at least two plates having at least one surface with a blood flow channel therein facing a surface with a collection channel therein separated by a semipermeable membrane selectively permeable to the blood fraction, an inlet for conducting blood to each blood flow channel and an outlet for conducting blood therefrom to establish a longitudinally extending blood flow path, each blood flow channel having a distribution portion for uniformly distributing blood transversely of the blood flow path and a transfer portion extending longitudinally thereof, said transfer portion of said blood flow channel being more narrow at the outlet thereof than at the inlet thereto sufficiently to maintain blood velocity substantially constant through said transfer portion, each collection channel being substantially in registry with said transfer portion of said facing blood flow channel for receiving the blood fraction passing through said membrane, and a fraction outlet for conducting the blood fraction from each collection channel, whereby the blood fraction continuously transfers from blood passing through said transfer portion of each blood flow channel through the membrane to the adjacent collection channel to said fraction outlet.

75. The device of claim 74, wherein said transfer portion of each blood flow channel is tapered from blood inlet to blood inlet to maintain blood flow velocity substantially constant as the blood fraction is transferred from the blood.

76. The device of claim 75, wherein each collection channel is complimentary in shape to said tapered transfer portion of said blood flow channels.

77. The device of claim 74, and further comprising means associated with each collection channel for minimizing transmembrane pressure.

78. The device of claim 74, wherein said blood inlet extends through the end surface of each plate having a blood flow channel therein and said blood outlet extends through the opposite end surface of said plate.

79. The device of claim 74, wherein each blood flow channel has a combining portion for conducting blood from said transfer portion to said blood outlet, said distribution and combining portions each comprising a multiple bifurcated manifold wherein the depth of each manifold increases from said transfer portion to said blood inlet or blood outlet.

80. The device of claim 74, and further comprising a blood inlet manifold connected to each blood inlet for distributing blood from a source thereof evenly among said inlets and a blood outlet manifold connected to each blood outlet for collecting blood therefrom combining same into a single stream and a blood fraction outlet manifold connected to each blood fraction outlet for collecting blood fractions therefrom.

81. The device of claim 74, wherein some plates have blood flow channels in both surfaces thereof.

82. The device of claim 74, wherein some plates have collection channels in both surfaces thereof.

83. A method of continuously fractionating blood in situ, comprising establishing a closed loop between the blood donor and a device having a blood inlet and outlet and a blood fraction outlet wherein the device has a low blood and blood fraction retention of less than about 10 mls, pumping blood from the donor to the blood inlet and through the device and from the blood outlet to the donor while continuously producing a blood fraction, maintaining the blood flow velocity substantially constant through the device during production of the blood fraction, collecting the blood fraction from the blood fraction outlet, and disconnecting the closed loop from the donor.

84. The method of claim 83, wherein the device is a stack of plates having channels therein and blood is uniformly distributed among some of the plate channels and the blood fraction is received in other of the plate channels, the blood channels being separated from the blood fraction channels by a membrane selectively permeable to the blood fraction.

85. The method of claim 83, wherein the blood flow rate is accelerated from the inlet of the device to the outlet.

86. The method of claim 83, wherein the transmembrane pressure is minimized during production of the blood fraction.

87. The method of claim 86, the blood fraction is plasma and the membrane has a pore size in the range of from about 0.1 and about 1.5 microns.

88. The method of claim 83, wherein an anticoagulant is added to the blood before the blood enters the blood inlet.

89. The method of claim 83, wherein the anticoagulant is citrated saline or heparinized saline.

90. The method of claim 84, wherein the blood flow rate is about 65 milliliters per minute and the anticoagulant flow rate is about 15 milliliters per minute and the anticoagulant is citrated or heparinized saline.

91. The method of claim 89, wherein the blood flow rate and the blood shear are maintained substantially constant from inlet to outlet.

92. A system for continuously producing a blood fraction in situ comprising a closed blood flow loop between a blood fraction donor and a fractionating device, a pump for pumping blood from the donor to said fractionating device and therefrom to the donor, said fractionating device comprising a stack of at least two plates having at least one surface with a blood flow channel therein facing a surface with a collection channel therein separated by a semipermeable membrane selectively permeable to the blood fraction, an inlet to said device connected to said closed loop for conducting blood to each blood flow channel and an outlet from said device connected to said closed loop for establishing a longitudinally extending blood flow path through said device, each blood flow channel having a distribution portion for uniformly distributing blood transversely of the blood flow path and a transfer portion extending longitudinally thereof, said transfer portion of said blood flow channel being more narrow at the outlet thereof than at the inlet thereto sufficiently to maintain blood velocity substantially constant through said transfer portion, each collection channel being substantially in registry with said transfer portion of said facing blood flow channel for receiving the blood fraction passing through said membrane, a fraction outlet for conducting the blood fraction from each collection channel, and a receptacle for storing the blood fraction, whereby the blood fraction continuously transfers to said receptacle from blood passing through said device during transit from and to the donor in said closed top.

93. The system of claim 92, wherein each collection channel is complimentary in shape to said tapered transfer portion of said blood flow channels.

94. The system of claim 92, and further comprising means associated with each collection channel for minimizing transmembrane pressure.

95. The system of claim 92, wherein said blood inlet extends through the end surface of each plate having a blood flow channel therein and said blood outlet extends through the opposite end surface of said plate.

96. The system of claim 92, wherein each blood flow channel has a combining portion for conducting blood from said transfer portion to said blood outlet, said distribution and combining portions each comprising a multiple bifurcated manifold wherein the depth of each manifold increases from said transfer portion to said blood inlet or blood outlet.

97. The system of claim 92, and further comprising a blood inlet manifold connected to each blood inlet for distributing blood from a source thereof evenly among said inlets and a blood outlet manifold connected to each blood outlet for collecting blood therefrom combining same into a single stream and a blood fraction outlet manifold connected to each blood fraction outlet for collecting blood fractions therefrom.

98. The system of claim 92, wherein some plates have blood flow channels in both surfaces thereof 99. The system of claim 92, wherein some plates have collection channels in both surfaces thereof.

100. The system of claim 92, and further including a source of anticoagulant connected to said closed loop between the donor and said fractionating device.

101. The system of claim 100, wherein the anticoagulant is citrated saline or heparinized saline.

102. The system of claim 100, wherein the blood fraction is plasma and the membrane has a pore size in the range of from about 0.1 microns to about 1.5 microns.

103. The system of claim 102, wherein the blood flow rate is about 65 milliliters per minute and the anticoagulant flow rate is about 15 milliliters per minute and the anticoagulant is citrated saline or heparinized saline.

104. The system of claim 102, wherein said transfer portion of each blood channel is tapered from inlet to outlet to maintain blood flow rate constant and each collection channel is shaped complimentary to said tapered transfer portion.

105. The system of claim 104, and further comprising means associated with each collection channel for minimizing transmembrane pressure.

106. The system of claim 105, wherein said means is a plurality of longitudinally extending shallow grooves.

* * * * *